United States Patent [19]

Takahashi

[11] 4,203,430
[45] May 20, 1980

[54] DEVICE FOR CONTROLLING CURVATURE OF AN END SECTION IN AN ENDOSCOPE

[76] Inventor: Nagashige Takahashi, Tokiwadai Green Haitsu 602, No. 28-10, Tokiwadai 3-chome, Itabashi-ku, Tokyo, Japan

[21] Appl. No.: 846,473

[22] Filed: Oct. 28, 1977

[30] Foreign Application Priority Data

Dec. 16, 1976 [JP] Japan ............................. 51/168782

[51] Int. Cl.² ............................................. A61B 1/00
[52] U.S. Cl. ........................................ 128/4; 74/422; 74/501.5 R; 403/43
[58] Field of Search ........................................ 128/4–8; 254/66, 95–97; 403/43–48, 112, 308, 57; 74/422, 501.5 R

[56] References Cited

U.S. PATENT DOCUMENTS

| | | | |
|---|---|---|---|
| 1,156,997 | 10/1915 | Hayes | 403/112 |
| 2,467,066 | 4/1949 | Wilson | 74/422 X |
| 2,525,805 | 10/1950 | Kirkpatrick | 74/422 X |
| 2,571,052 | 10/1951 | Mount | 403/57 |
| 2,822,199 | 2/1958 | Johnson | 403/45X |
| 3,256,875 | 6/1966 | Tsepeleu et al. | 128/8 |
| 3,551,959 | 1/1971 | Mastalski | 403/43 |
| 3,892,228 | 7/1975 | Mitsui | 128/4 |

FOREIGN PATENT DOCUMENTS

548462 10/1942 United Kingdom ..................... 128/8

Primary Examiner—Edgar S. Burr
Assistant Examiner—Steven A. Bratlie
Attorney, Agent, or Firm—Sughrue, Rothwell, Mion, Zinn and Macpeak

[57] ABSTRACT

A device for controlling the curvature of an end section in an endoscope is provided with tension control members for regulating the tensions in the actuating wires and adjustment members for defining the maximum movement of the end section. The end section is connected by two wires extending through a flexible pipe to a manual operating section. The manual operating section has a knob by means of which a pinion gear is rotated. The pinion gear meshes with two parallel rack gears. The two wires are respectively connected to one of the ends of each of the two rack gears by means of the tension control members. Each tension control member includes a wire stopper secured to a corresponding wire end and a wire control cylinder engagable with the wire stopper but allowing the wire stopper to be freely movable within the wire control cylinder when the wire is slack. The wire control cylinders are threaded onto bolts extending from the rack gears. The adjustment members are limit screws at the opposite ends of the rack gears.

3 Claims, 2 Drawing Figures

DEVICE FOR CONTROLLING CURVATURE OF AN END SECTION IN AN ENDOSCOPE

BACKGROUND OF THE INVENTION

This invention relates to a curvature control device for elevating the end section of an endoscope which is inserted into a part to be examined. The specific features of the invention reside especially in the control of the amount of play in curving the end section and in a curvature operation range control mechanism thereof.

In general, in a curvature control device for an endoscope of this type, the aforementioned end section is coupled through two wires to a mannual operating section, and the end section is curved to either side by selectively pulling one of the two wires. In this case, the other wire must extend or contract depending on the curvature of the end section. Therefore, there must be provided an idle mechanism between the wires and the operating mechanism in order to absorb the difference between the amount of wire movement and the amount of the pulling operation.

On the other hand if, with respect to the movement of the wire which is tightened by being pulled in order to determine the direction and degree of the curvature of the end section, there is play in the pulling operation due to the wire tension, the delicate sense of the operator's hand is affected, which may lead to erroneous operations such as for instance a mistake in finding the part to be examined. Accordingly, the play must be minimized.

There are some devices which have been improved so as to meet the various requirements for eliminating the above-described difficulties. However, even with such improved devices, the wires are liable to be lengthened and the relevant operating members are deformed by repeatedly using the devices for a long time. Therefore, the actual amount of movement of the wire is liable to be changed over a period of time when compared with the amount of movement thereof obtained when it was initially used. Therefore, it is necessary to eliminate the amount of play by adjusting the relevent mechanisms when required.

If the wire has play (the actual amount of movement of the wire is decreased by the lengthening of the wire), with the operation range of the operating member preset the curvature range of the end section is decreased, the observation range is also decreased, and it may be difficult to sample desired cells. Accordingly, adjustment of the operation range of the operating member is necessitated to eliminate the play which is caused by using the device for a long time.

In the case of the conventional device of this type, in order to eliminate the play which is caused by the use of the device, a method in which the length of the wire is shortened or the coupling positions and angles between the operating knob and the movable members are readjusted, that is, a method of disassembling the relevant mechanisms, is employed. This work is difficult and troublesome.

SUMMARY OF THE INVENTION

Accordingly, an object of this invention is to eliminate all of the drawbacks accompanying the conventional devices as described above. More specifically, an object of the present invention is to provide a curvature control device in which repairs of such as for instance absorption of play can be readily achieved by simple external adjustments.

The foregoing and other objects of the invention are attained by providing tension control members for adjusting the tensions in the actuating wires and adjustment members for defining the maximum movement of the end section. In a preferred embodiment, the manual operating section has a knob by means of which a pinion gear meshes with two parallel rack gears. These rack gears move or slide in opposite directions when the knob is rotated. The two wires are respectively connected to one of the ends of each of the two rack gears by means of the tension control members. Each tension control member includes a wire stopper secured to a corresponding wire end and a wire control cylinder engagable with the wire stopper but allowing the wire stopper to be freely movable within the wire control cylinder when the wire is slack. The wire control cylinders are threaded onto bolts extending from the rack gears. By rotating the wire control cylinders in one direction or the other, the tensions of the wires can be regulated. At the same time the free movement of the wire stoppers inside their respective wire control cylinders provides an idle mechanism. The adjustment members are limit screws at the opposite ends of the rack gears. The ends of the limit screws are in facing abutment with the ends of the racks so that by a simple external adjustment of the limit screws, the maximum movements of the rack gears, and hence the curvable end section, can be adjusted.

BRIEF DESCRIPTION OF THE DRAWING

By way of example only, the preferred embodiment of the invention will be described with reference to the accompanying drawing in which.

DETAILED DESCRIPTION OF THE INVENTION

Figure 1:
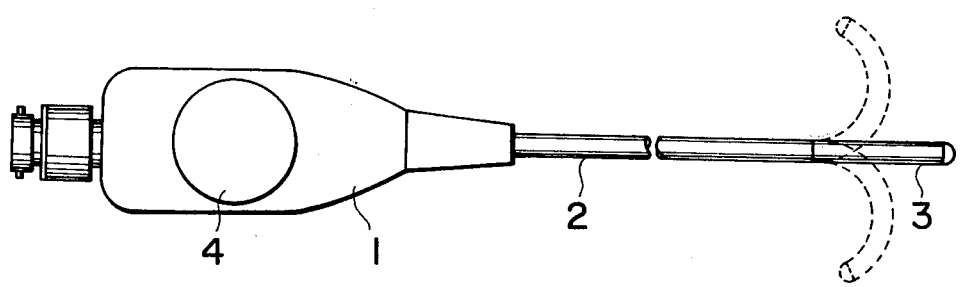
FIG. 1 is a side view of an endoscope according to the invention.

FIG. 1 is a side view illustrating the external appearance of an endoscope. In FIG. 1, an end section 3 which is inserted into a part to be examined is connected through a flexible connecting pipe 2 to a manual operating section 1. The endoscope is so designed that the end section 3 is elevated upward and downward by rotating an operating knob 4 provided on the manual operating section 1.

Figure 2:
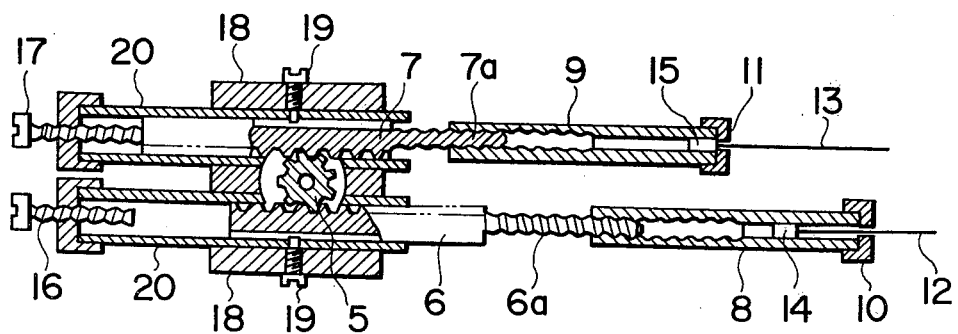
FIG. 2 is a detailed view, partly in section, illustrating the specific features of the invention.

FIG. 2 is a detailed view, partly in section, showing essential components of the preferred embodiment of the invention. In FIG. 2, a pinion 5 is rotated by the operating knob 4. Two rack gears 6 and 7 arranged in parallel mesh with the pinion 5 so that they are moved in opposite directions when the knob 4 is rotated. A bolt 6a is secured to one end of the rack gear 6, and a corresponding bolt 7a is secured to one end of the rack gear 7. Wire control cylinders 8 and 9 are internally threaded so as to engage the aforementioned bolts 6a and 7a, respectively. Closing crowns 10 and 11 each having a small hole at the center are screwed on the other ends of the wire control cylinders 8 and 9, respectively. Actuating wires 12 and 13 operatively connect the operating knob 1 to the end section 3. One end of each of the wires is fixedly secured to the corresponding edge of the end section 3, while the other end thereof is also fixedly secured to a respective one of wire stoppers 14 or 15 after being passed through the corresponding small hole in the closing crown 10 or 11.

Adjustable limit screws 16 and 17 are provided in the movement regions of the racks 6 and 7 in such a manner that the limit screws are externally operated to be screwed in or out. The ends of the limit screws 16 and 17 are allowed to abut against the ends of the rack gears 6 and 7 so that the operation range of the rack gears and accordingly the range of rotating operation angle of the operating knob 4 is adjusted. In addition, a gear box 18 fixedly secures the aforementioned operating sections to the manual operating sections, and the screws 19 are adapted to secure rack guides 20 and to stop the rotation of the rack gears 6 and 7.

In the device thus organized according to this invention, in adjusting the bending operation mechanism the rotating operation range of the operating knob 4 is first determined by adjusting the positions of the limit screws 16 and 17 where the limit screws are allowed to abut against the ends of the rack gears 6 and 7. Then, the operating knob 4 is rotated in one direction to move the rack gears 6 and 7. In this case, under the condition that one of the rack gears 6 and 7, that is, the rack gear 7 for instance is maximally moved, or abutted against the limit screw 17 as shown in FIG. 2, the control cylinder 9 threaded on the bolt 7a of the rack 7 is turned so that the control cylinder 9 is moved forward or backward with respect to the position of the rack gear 7 thereby regulating the tension of the actuating wire 13 which is locked with the closing crown 11 and the wire stopper 15 so as to maximize the curvature, in one direction, of the end section 3 which is curved by the tension of the wire 13.

After completion of this adjustment of the curvature in one direction of the end section 3, the operating knob 4 is turned in the opposite direction. Then, similarly as in the above-described adjustment, the position of the control cylinder 8 is adjusted so as to regulate the tension of wire 12 and hence the curvature, in the opposite direction, of the end section 3.

Through these adjustments, the operation range of the operating knob 4 is limited by the positions of the adjustment of limit screws 16 and 17 which abut against the ends of the two rack gears 6 and 7 as they are moved in the opposite directions. This adjustment is such that the curvature of the end section 3 is coarsely adjusted by the tensions of the actuating wires 12 and 13. However, the tensions of the wires 12 and 13 and accordingly the curvature of the end section 3 is finely adjusted by means of the control cylinders 8 and 9. Therefore, the end section is elevated upward and downward by the operation of the operating knob 4 suitably without operation play.

In the elevation of the end section 3 by pulling one of the wires 12 or 13, the other wire 13 or 12 not under tension can freely move along the hollow part in the control cylinder 9 or 8 because its wire stopper 15 or 14 can move away from the closing crown 11 or 10. Therefore, the end section curving operation can be carried out very smoothly.

Furthermore, the adjustments can be determined only by the wire tensions, that is, only taking into account the maximum curvature without paying attention to the play of the wire which may be caused by stretching the wire. Therefore, the necessary adjustment can be readily and suitably carried out. In addition, according to this invention, the limit screws 16 and 17 for adjusting the operation range of the operating knob 4 and the control cylinders 8 and 9 for finely adjusting the curvature of the end section 3 can be directly adjusted by removing the outer case of the manual operating section 1. Therefore, the undesirable play in operation which may be caused by the use thereof with the lapse of time can be readily corrected when required.

What is claimed is:

1. In an endoscope of the type having a curvable end section adapted to be inserted into a part to be examined, a flexible connecting pipe connecting the curvable end section to a manual operating section, and two actuating wires extending through the flexible connecting pipe and connecting the curvable end section to a device in the manual operating section for controlling the curvature of the curvable end section, said device comprising:

an angle operating knob and two parallel sliding members, said angle operating knob being operatively coupled to said two sliding members so that rotation of said angle operating knob produces movements of said two sliding members in opposite directions, tension control members attaching said two wires to respective ones of said two sliding members, said tension control members being adjustable to regulate the tensions of said two wires, and adjustment members provided in the movement ranges of said two sliding members and adjustable to define the maximum movement positions of said two sliding members.

2. The device as claimed in claim 1, wherein each of said tension control members comprises:

a wire stopper fixedly secured to the pull side end of a respective actuating wire, and a wire control cylinder engagable with said wire stopper at one end portion thereof but allowing free movement of said wire stopper within said cylinder when the corresponding wire is slack, said wire control cylinder being threadably attached to a respective sliding member so that the tension of the corresponding wire may be regulated by rotating said wire control cylinder.

3. The device as claimed in claim 1 wherein said two parallel sliding members are rack gears which mesh with a pinion gear rotated by said angle operating knob, said adjustment members being limit screws the adjustment of which is external to said device, said limit screws being positioned so that they face the ends, in a wire pulling direction, of said rack gears, the maximum movement positions of said rack gears being limited by allowing the ends of said limit screws to abut against the ends of said rack gears.

* * * * *